United States Patent [19]
Craggs

[11] Patent Number: 5,478,305
[45] Date of Patent: Dec. 26, 1995

[54] PROSTHETIC SPHINCTER DEVICE

[75] Inventor: Michael D. Craggs, London, England

[73] Assignee: British Technology Group Group Limited, London, England

[21] Appl. No.: 256,030

[22] PCT Filed: Feb. 3, 1993

[86] PCT No.: PCT/GB93/00223

§ 371 Date: Jun. 22, 1994

§ 102(e) Date: Jun. 22, 1994

[87] PCT Pub. No.: WO93/14717

PCT Pub. Date: Aug. 5, 1993

[30] Foreign Application Priority Data

Feb. 3, 1993 [GB] United Kingdom .................. 9202247

[51] Int. Cl.$^6$ ........................................................ A61F 2/00
[52] U.S. Cl. ........................................ 600/31; 128/DIG. 25
[58] Field of Search ................. 600/29–32; 128/DIG. 25

[56] References Cited

U.S. PATENT DOCUMENTS

| | | | |
|---|---|---|---|
| 4,256,093 | 3/1981 | Helms et al. | 600/31 |
| 4,682,583 | 7/1987 | Burton et al. | 600/31 |
| 4,829,990 | 5/1989 | Thuroff et al. | |
| 4,958,630 | 9/1990 | Rosenbluth et al. | |

FOREIGN PATENT DOCUMENTS

| | | |
|---|---|---|
| 265207 | 4/1988 | European Pat. Off. . |
| 0348114 | 12/1989 | European Pat. Off. . |
| 407218 | 1/1991 | European Pat. Off. . |
| 0409592 | 1/1991 | European Pat. Off. . |
| 2373272 | 7/1978 | France . |
| 2174911 | 11/1986 | United Kingdom . |
| 8900030 | 1/1989 | WIPO ................................ 600/29 |

*Primary Examiner*—Angela D. Sykes
*Assistant Examiner*—John P. Lacyk
*Attorney, Agent, or Firm*—Cushman, Darby & Cushman

[57] ABSTRACT

The present invention relates to an implantable prosthetic sphincter device defining a closed pressure-fluid system operable by a recipient to control a body duct. The device includes an inflatable cuff (10), a fluid reservoir (11), and pump and control assembly (12) for deflating the cuff and controlling its reinflation. The pump and control assembly (12) includes an elastomeric sleeve (23) resiliently engaged around a bead (24, 25) normally to effect a fluid seal therebetween, with such engagement being selectively deformable to allow fluid flow between the elastomeric sleeve (23) and the bead (24, 25). A one-way valve (35) is provided to prevent flow directly from the pump volume (22) to the cuff (10). The bead engagement within the elastomeric sleeve (23) may form a valve between the reservoir (11) and the cuff (10) and/or between the pump volume (22) and the reservoir (11). The invention has applications in controlling urinary or faecal incontinence.

20 Claims, 2 Drawing Sheets

PROSTHETIC SPHINCTER DEVICE

BACKGROUND OF THE INVENTION

This invention concerns prosthetic sphincter devices and, more particularly, such devices of the kind comprising a closed pressure-fluid system operable by the recipient to control a body duct.

Prior devices of this kind can be seen to involve in common four basic component parts, namely, a reservoir for the pressure fluid, an inflatable duct-obturating means, a pump facility operable by the recipient to inflate and/or deflate the obturating means, and a control mechanism for the pump facility, interconnected by tubing. Typically the device is wholly implantable, the pump facility is located subcutaneously for operation by palpation, and the obturating means is a cuff locatable around the urethra or other appropriate site to act against urinary incontinence when inflated and to allow urination when deflated.

In an earlier form of these devices, the pump facility and control mechanism comprise separate pumps connected, by way of valves, between the reservoir and cuff respectively for inflation and deflation. The valves are essentially of unidirectional flow type to direct the pumped fluid appropriately, and also serve a pressure relief function to ensure that the cuff is not inflated above a preset pressure level.

In a subsequently developed form of the devices in question there is a single pump connected, by way of the control mechanism, between the reservoir and cuff to deflate the latter. In this case the reservoir serves to hold fluid at a preset pressure and the control mechanism allows a restricted flow to the cuff to maintain the same normally inflated at such pressure.

It will be appreciated that the devices available are not without certain disadvantages. They are frequently relatively complex, requiring a number of mechanical parts, all of which may be subject to mechanical failure or failure to function correctly.

SUMMARY OF THE INVENTION

It is an object of the present invention to provide a prosthetic sphincter device for use in incontinence control, to be surgically implantable and controllable from the exterior of the recipient's body, which features a very simple, reliable and resilient operating mechanism and thus reduces the possibility of unsatisfactory operation or mechanical failure.

According to the present invention there is provided a prosthetic sphincter device operable by a recipient to control a body duct, the device comprising in operable interconnection inflatable fluid-operated occlusion means for closing said body duct;

a fluid reservoir;

pump means in fluid communication with said occlusion means and said fluid reservoir for transferring fluid from said occlusion means to said fluid reservoir to deflate said occlusion means and thereby open said body duct; and control means connected in parallel with said pump means and arranged to maintain said occlusion means normally inflated;

characterised in that at least one of said pump means and said control means includes an elastomeric sleeve resiliently engaged around a bead normally to effect a fluid seal therebetween, with such engagement being selectively deformable to allow fluid flow between the elastomeric sleeve and the bead.

Preferably said elastomeric sleeve is part of a deformable bulb and said engagement between said elastomeric sleeve and said bead forms a normally closed valve in a fluid passage between the pump means and the fluid reservoir.

Preferably said bead is provided with a bore for fluid communication between said pump means and said occlusion means, a one-way valve being provided to prevent flow through the bore from said pump means to said occlusion means.

In a preferred form of the embodiment, the one-way valve comprises a ball valve.

Preferably the bead or a further bead is resiliently engaged within said elastomeric sleeve normally to effect a fluid seal therebetween, this latter engagement providing a selectively operable valve between said fluid reservoir and said occlusion means.

In a preferred form of the embodiment a leakage path is provided between the fluid reservoir and the occlusion means, preferably including a throttle opening in a wall of a fluid passage to said fluid reservoir and a thin elastomeric sleeve resiliently mounted around said fluid passage to cover said throttle orifice.

Preferably a self-sealing diaphragm is provided to allow flow of said fluid therethrough by way of an injection instrument.

The prosthetic sphincter device of the invention features a very simple and reliable operating mechanism. The fluid passage from the pump means to the fluid reservoir is automatically opened by operating the pump means due to the deformation of the elastomeric sleeve around the bead, thereby allowing the passage of fluid between the two. A single one-way valve is required to prevent the passage of fluid from the pump means to the inflatable occlusion means. Previous devices have used more than one such valve or valves of relatively complex design.

BRIEF DESCRIPTION OF THE DRAWINGS

Certain embodiments of the invention will now be described by way of example with reference to the accompanying drawings, in which.

DETAILED DESCRIPTION OF A PREFERRED EMBODIMENT

Figure 1:
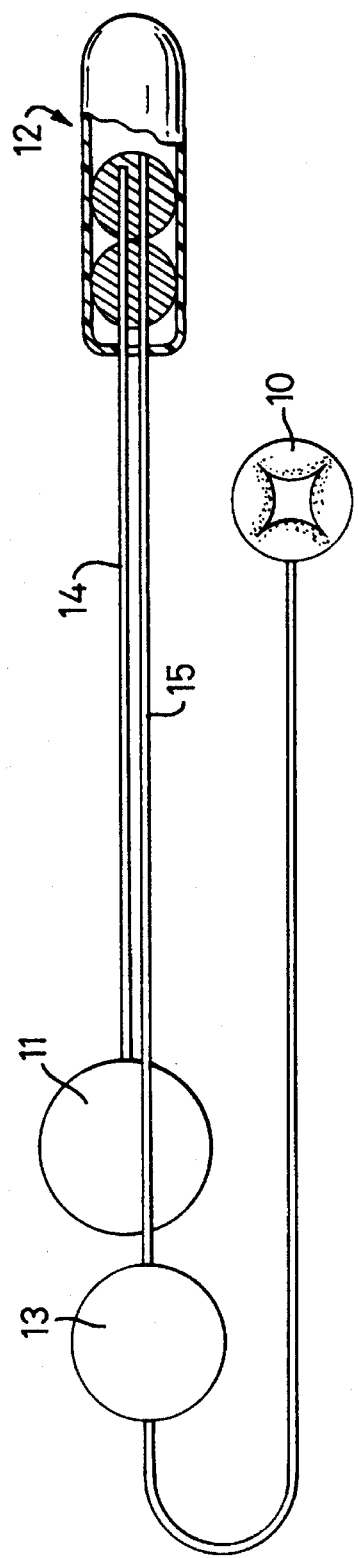
FIG. 1 illustrates one embodiment of a prosthetic sphincter device according to the present invention.

In FIG. 1 the principal components of the prosthetic sphincter device for use in controlling urinary incontinence are shown. An inflatable cuff 10 serving as an occlusion means for fitting around the body duct is provided, such that as fluid pressure to the cuff increases the cuff inflates to close the body duct. A fluid reservoir in the form of an elastomeric regulating balloon 11 serves as a variable volume chamber and is able to displace a fluid volume greater than that necessary to maintain the cuff inflated. Pump and control means 12 are provided to operate the device and these will be described in greater detail later on with reference to FIG. 2.

The pump and control means 12 are connected to the regulating balloon 11 by means of a first flexible tube 14 and to the cuff 10 by means of a second flexible tube 15.

A stress balloon 13 is also provided in series with the cuff 10 in order to transmit transient intra-abdominal pressure rises directly to the cuff 10 and thereby prevent leakage through the body duct during coughing or other straining (so-called stress incontinence).

Figure 2:
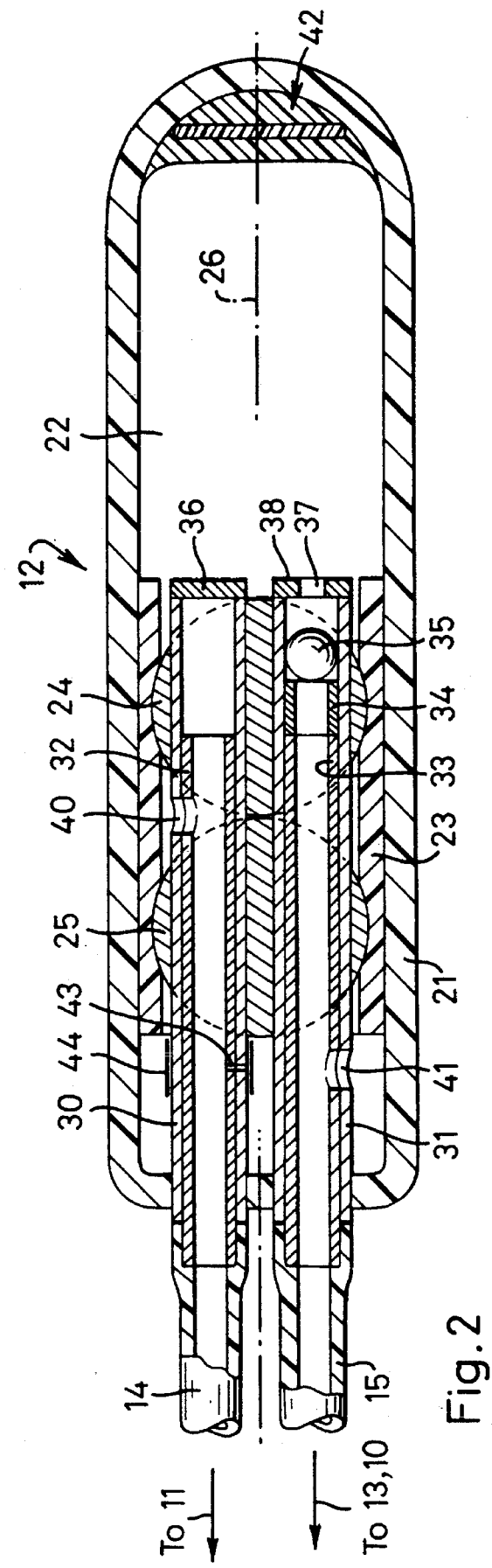
FIG. 2 illustrates a cross section of the pump and control means used in the device of FIG. 1.

FIG. 2 illustrates in detail the pump and control means 12 according to the invention. These are enclosed within an elongated elastomeric bulb 21. One end of this bulb forms the pump, which is operable by simple squeezing of the bulb around pump volume 22, and is in fluid communication with flexible tubes 14 and 15 via the control means.

The control means includes first and second spherical beads 24 and 25 made of a non-deformable material. The beads 24 and 25 are arranged longitudinally of one another and are contained tightly in sealing engagement within a cylindrical deformable elastomeric sleeve 23 which fits against the inner wall of the bulb 21 and is fixed thereto. This sleeve 23 extends around the beads but does not extend into the region of the bulb containing the pump volume 22. As shown in FIG. 2, each bead 24,25 features two parallel bores symmetrically located about the longitudinal center line 26 of the bulb 21, and longitudinally aligned from one bead to the other. The bores are sized to accommodate straight tubes 30 and 31 which pass through the two beads 24 and 25 and are preferably fixed in place in sealed engagement within the beads. These tubes 30 and 31 extend from outside the end wall of elastomeric bulb 21 at the opposite end of the bulb to that of the pump volume 22, into the interior of the bulb and through the length of the parallel bores in the beads 24 and 25. The tubes are fixed in sealed engagement where they pass through the end wall of elastomeric bulb 21. The tubes 30 and 31 terminate just beyond the surface of the first bead 24 on the side of the pump volume 22 where they are sealed closed by disc-shaped end walls 36 and 38 respectively. An orifice 37 is provided in the end wall 38 in line with the end of tube 31 to provide free fluid communication between the pump volume and the interior of tube 31 at this point.

Within these tubes 30 and 31 are located inner tube portions 32 and 33 respectively which are offset longitudinally from the tubes 30 and 31. The inner tube portions 32 and 33 extend beyond the ends of tubes 30 and 31 externally of bulb 21 and the flexible tubes 14 and 15 are connected to tube portions 32 and 33 at this end, thereby providing fluid communication between the interior of tubes 30 and 31 and the cuff 10 and regulating balloon 11 respectively.

In the region within tube 31 between the end of tube portion 33 and end wall 38, a one-way valve comprising a ball 35 and an annular sealing valve seat 34 is provided. The valve seat 34 is fixed against the end of tube portion 33 and the ball is confined between this valve seat 34 and the end wall 38.

The one-way valve prevents fluid from flowing from the pump volume 22 directly into flexible tube 15, allowing free fluid communication only in the direction from the cuff 10 to the pump volume 22, that is to say, from left to right as shown in FIG. 2. The pump is therefore provided by the combination of the pump volume 22 and the one-way ball valve 35.

The control means also features two ports 40 and 41. Port 40 is formed at a coincident point in the walls of tube 30 and inner tube portion 32 and is located between the two beads 24 and 25, whilst port 41 is formed at a coincident point in the walls of tube 31 and inner tube portion 33 and is located between the second bead 25 and the end of the bulb distant from the pump volume 22. These ports provide unrestricted fluid communication between the interior and the exterior of the tube portions at those points.

The elastomeric bulb 21 further features a self-sealing diaphragm 42 in the pump end to allow for extra fluid to be introduced into the device by means of a syringe, or to allow for fluid to be withdrawn from the device, if the operating pressure is to be varied or if minor leakage from the device should occur. This self-sealing diaphragm 42 also allows for the pressure within the prosthetic sphincter device to be monitored to check the functioning of the device when surgically implanted within the patient's body. Such diaphragms are known within the general medical field and will not be described in greater detail here.

When implanted, the cuff 10 is fitted around the urethra of the patient, the regulating balloon 11 and the stress balloon 13 are located within the abdominal cavity, and the pump and control means 12 are located within the scrotum or labia.

In operation the user manipulates the bulb 21 through the skin of the scrotum or labia by palpation to deflate or inflate the cuff 10. By squeezing on the end of the elastomeric bulb enclosing pump volume 22 the fluid pressure in this region rises sharply but the fluid is prevented from passing into the flexible tube 15 connected to the cuff 10 by one-way ball valve 35. Instead the pressure causes some deformation of the elastomeric sleeve 23 around the first bead 24 allowing the fluid to pass around the bead 24 and into the region between the two beads 24 and 25. The fluid then passes through the port 40 and into the interior of tube 30 and tube portion 32 and from there to the regulating balloon 11 through flexible tube 14. On releasing the pump the partial vacuum created draws fluid from the cuff through flexible tube 15, across one-way ball valve 35 and through the orifice 37. Further squeezing and releasing of the pump will deflate the cuff 10 as far as is necessary to open the urethral passage and allow the user to urinate.

When urination is completed the user squeezes the elastomeric bulb 21 in the region around the second bead 25. The elastomeric material used in sleeve 23 is such that this action will deform the sleeve sufficiently to allow fluid to pass between the bead 25 and the sleeve 23. This forms a fluid connection between ports 40 and 41 and thus between the regulating balloon 11 and the cuff 10, allowing the pressure of the regulating balloon to reinflate the cuff and occlude the urethral passage once again. Manipulation of this 'squeeze- valve' is very simple through the walls of the elastomeric bulb 21, but if the same action also allows fluid to pass between the first bead 24 and the sleeve 23 this is quite acceptable since the fluid pressure will still equalise throughout the device.

It is evident that this device requires very few moving components. Apart from the valving arrangement formed by the engagement of the elastomeric sleeve 23 around the non-deformable beads 24 and 25, the only valve in the device is the one-way ball valve 35.

A further feature is also illustrated in FIG. 2, where a restricted unidirectional flow valve is provided between the cuff 10 and the regulating balloon 11. This comprises a throttle orifice 43 in tube 30 and tube portion 32 in a section between the second bead 25 and the end wall of the bulb 21 distant from the pump volume 22. The tube portion 32 is closely sheathed in this section with a thin elastomeric membrane 44 covering the throttle orifice 43 such that fluid can leak back from the regulating balloon 11 via flexible tube 14, throttle orifice 43, port 41 and flexible tube 15, to reinflate the cuff 10 slowly and automatically after pumped deflation. The elastomeric membrane 44 ensures that the fluid flow is unidirectional to prevent particular stresses on the inflated cuff 10 from forcing fluid back into the regulating balloon 11 thus partially deflating the cuff and allowing leakage through the urethral passage when the stress is removed. These particular stresses may result from activities of the user such as riding a bicycle. The dimensions of the throttle orifice 43 and the dimensions and material of the membrane 44 are selected to provide the required recovery time for the cuff 10 to reinflate.

The restricted unidirectional flow valve may be included in the device along with the squeeze-valve constituted by bead 25 and elastomeric sleeve 23, where the user may decide either to allow the cuff 10 to reinflate slowly and automatically, or to use the squeeze-valve to bypass the restricted flow valve and thereby directly and more rapidly reinflate the cuff. Alternatively, the control means may feature one or other of the valves depending on the circumstances or requirement of the surgeon or recipient.

The cuff 10, balloons 11 and 13, and flexible tubes 14 and 15 are preferably manufactured from medical grade clear silicon rubber for implantation, the cuff being reinforced. In addition, the elastomeric bulb 21 enclosing pump and control means, as well as the sleeve 23, are made from similarly physiologically inert material with appropriate elastomeric qualities, such as silicon rubber. The tube portions 30, 31, 32 and 33, and the end walls 36 and 38, are manufactured from a more rigid plastics material, such as polypropylene. This material is also suitable for manufacturing the beads 24 and 25. The ball 35 in the one-way valve is preferably made from a rigid material, and a small sapphire bead has been found to be suitable for this purpose. The sealing valve seat 34 is made from an appropriate rubber material.

The operation fluid used in the device is an isotonic hydraulic fluid in which a radio-opaque dye is preferably included to enable monitoring of the fluid using X-ray techniques during normal operation. In the unlikely event of any problems developing such techniques can also be used to monitor possible fluid leakage.

The device can be supplied in a sterilised pack as a single unit for implantation, pre-filled to a certain pressure, such as 1 atmosphere, with the working fluid. The surgeon subsequently needs only to add fluid up to the required pressure through the self-sealing membrane 42 incorporated in the device. Alternatively the various components can be supplied as a kit of separate parts, allowing substitution of parts if required. For example, cuffs of different sizes can be used according to the specific requirements.

Figure 3:
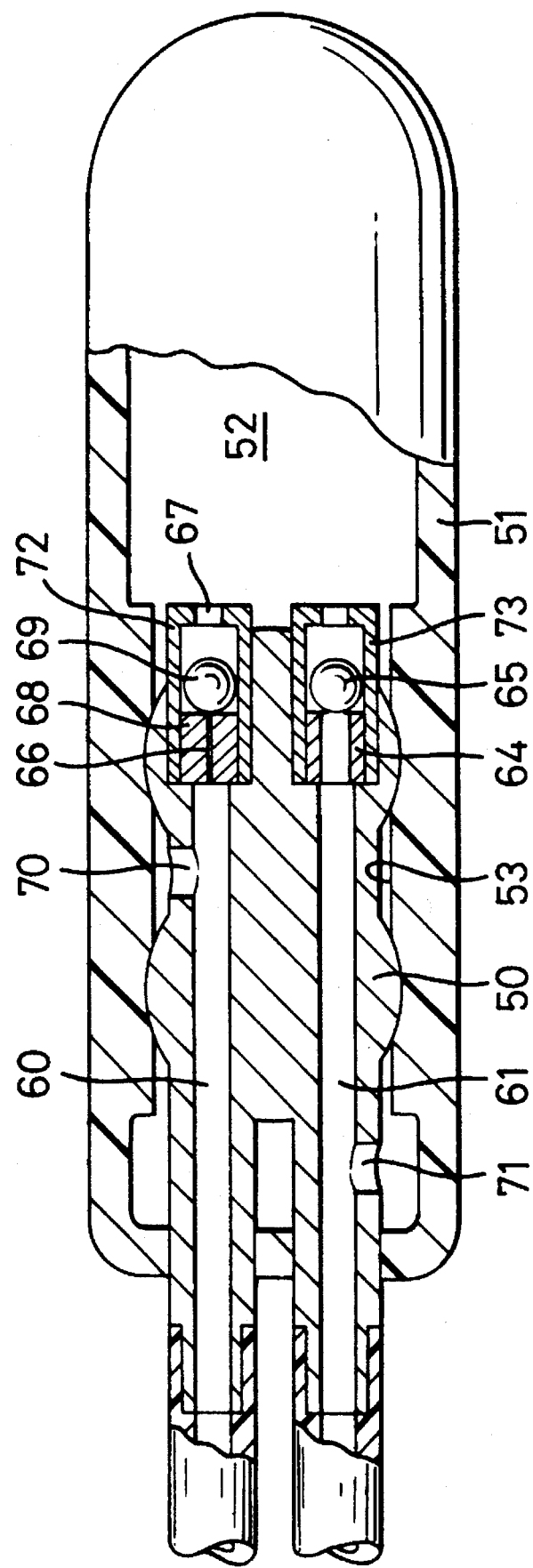
FIG. 3 illustrates a cross section of an alternative embodiment of the device.

A second embodiment of the pump and control means 12 is shown in cross section in FIG. 3. This dispenses with the separate tubes and tube portions 30, 31, 32, 33 and the twin beads 24, 25, and instead employs an integrally moulded bead 50. This bead 50 has an external profile providing the squeeze valves and has internal passages 60, 61 and openings 70, 71 to provide the fluid flow paths. Internal passage 60 is in connection with the regulating balloon 11, whilst internal passage 61 is in connection with the cuff 10. The bead 50 is resiliently engaged within the elastomeric sleeve 53 normally to effect a fluid seal therebetween.

The advantage of this embodiment resides in the fact that although the bead 50 requires a special moulding, the pump and control means comprise only two principal components; an elastomeric bulb 51, of which the elastomeric sleeve 53 forms an integral thickened part, and moulded bead 50.

Once again the elastomeric bulb 51 is preferably made from silicon rubber and the single bead 50 from polypropylene.

FIG. 3 also illustrates an alternative form of the restricted unidirectional flow valve providing the slow leakage path to reinflate the cuff after urination. The fluid flow passage 60 terminates in a valve housing 72 similar to the housing 73 of the on-way ball valve 64, 65 in the other passage 61. This housing 72 also features a valve seat 68 and a ball 69. An orifice 67 connects the valve housing 72 with the pump volume 52. The valve seat 68 provides only a very narrow fluid passage 66 which acts in the same way as the throttle orifice 43 in FIG. 2, whilst the ball 69 ensures that the function of this valve is unidirectional. After deflation of the cuff, the fluid in the regulating balloon 11 can slowly leak back through passage 60, throttle passage 66, orifice 67, and past one-way valve 64, 65 into passage 60 to reinflate the cuff. The one-way valve 64, 65 does not close during this operation because of the very low pressure of the fluid as it leaks back from the regulating balloon.

The advantage of this form of the restricted unidirectional flow valve is the resulting symmetrical form of the bead 50. Apart from the valve seat 68 with its narrow throttle passage 66, the one-way valve 64, 65 and the restricted unidirectional flow valve 68, 69 are identical, thus considerably simplifying the manufacture of the control means.

Alternative unidirection valves are of course possible within the scope of the invention, and the ball valves 34, 35; 64, 65 and 68, 69 may be replaced by, for example, membrane flap valves. This would have the advantage that the one-way valves could be manufactured as an integral part of the bead or beads of the control means. In the embodiment represented in FIG. 3, for example, the two on-way valves could be replaced by flap valves moulded or machined as an integral part of the single bead 50.

The embodiments of the invention illustrated in FIGS. 1, 2 and 3 and described above are given by way of example only and it should be understood that these in no way limit the cope of the invention, which is intended to embrace all embodiments that fall within the spirit and scope of the appended claims.

The invention has been conceived and developed for use in controlling urinary incontinence, but may have other applications in the medical field, such as use in controlling faecal incontinence.

I claim:

1. A prosthetic sphincter device operable by a recipient to control a body duct, the device comprising in operable interconnection:

inflatable fluid-operated occlusion means for closing said body duct;

a fluid reservoir;

pump means in fluid communication with said occlusion means and said fluid reservoir for transferring fluid from said occlusion means to said fluid reservoir to deflate said occlusion means and thereby open said body duct; and control means connected in parallel with said pump means for maintaining said occlusion means normally inflated;

at least one of said pump means and said control means including an elastomeric sleeve and a bead, the sleeve being resiliently engaged around the bead normally to effect a fluid seal therebetween, the bead being held in a fixed position within the sleeve and the sleeve being selectively deformable to allow fluid flow between the sleeve and the bead.

2. A device according to claim 1 wherein said elastomeric sleeve is an integral part of a deformable bulb and said engagement between said elastomeric sleeve and said bead forms a normally closed valve in a fluid passage between the pump means and the fluid reservoir.

3. A device according to claim 2 wherein said bead is provided with a bore for fluid communication between said pump means and said occlusion means, a one-way valve being provided to prevent flow through the bore from said pump means to said occlusion means.

4. A device according to claim 3 wherein said one-way valve comprises a ball valve.

5. A device according to claim 1 wherein said bead is resiliently engaged within said elastomeric sleeve normally to effect a fluid seal therebetween, this latter engagement providing a selectively operable valve between said fluid reservoir and said occlusion means.

6. A device according to claim 2, 3 or 4 wherein a further bead is resiliently engaged within said elastomeric sleeve normally to effect a fluid seal therebetween, this latter engagement providing a selectively operable valve between said fluid reservoir and said occlusion means.

7. A device according to claim 1 wherein a restricted unidirectional fluid communication is provided between said fluid reservoir and said occlusion means to allow fluid to leak from said fluid reservoir to said occlusion means.

8. A device according to claim 7 wherein the restricted unidirectional fluid communication includes a fluid passage having a wall and a throttle orifice in the wall of said fluid passage and a thin elastomeric sleeve resiliently mounted around said fluid passage to cover said throttle orifice.

9. A device according to claim 7 wherein the restricted unidirectional fluid communication includes a one-way ball valve and a throttle orifice, by way of which a fluid passage connects said fluid reservoir with said pump means.

10. A device according to claim 1 further comprising a self-sealing diaphragm incorporated in a wall of a part of the device to allow flow of fluid into and out of the device by way of an injection instrument.

11. A prosthetic sphincter device operable by a recipient to control a body duct, the device comprising:

inflatable fluid-operated occlusion means for closing said body duct;

a fluid reservoir;

pump means in fluid communication with said occlusion means and said fluid reservoir for transferring fluid from said occlusion means to said fluid reservoir to deflate said occlusion means and thereby open said body duct; and control means connected in parallel with said pump means for maintaining said occlusion means normally inflated;

said pump means and said control means comprising an elastomeric bulb and two beads, the elastomeric bulb having respective sleeve portions, the two beads being resiliently engaged independently of one another within the elastomeric bulb normally to effect fluid seals between said sleeve portions and said beads, the respective sleeve portions being individually selectively deformable to allow fluid flow between said sleeve portions and said beads, the elastomeric bulb also enclosing a pump volume closed by a first one of said beads, the beads provided with bores, and a fluid passage running respectively through said bores, a first one of said fluid passages connecting said pump volume with said occlusion means by way of a one-way valve arranged to prevent fluid flow therethrough to said occlusion means, and a second one of said fluid passages having a wall and connecting said fluid reservoir with an opening into a space between the two beads, a further opening being provided in the first fluid passage such that the engagement between the second one of said beads and its respective sleeve portion forms a selectively operable valve between said fluid reservoir and said occlusion means, whilst the engagement between said first bead and its respective sleeve portion forms a selectively operable valve between said pump volume and said fluid reservoir.

12. A device according to claim 11 wherein said beads are integral parts of a single body contained within said elastomeric bulb.

13. A device according to claim 11 or 12 wherein said one-way valve comprises a ball valve.

14. A device according to claim 11, wherein a fluid leakage path is provided from said fluid reservoir to said occlusion means.

15. A device according to claim 14 wherein said leakage path includes a throttle orifice in the wall of said second fluid passage and a thin elastomeric sleeve resiliently mounted around said second fluid passage to cover said throttle orifice.

16. A device according to claim 14 wherein said leakage path includes a one-way ball valve and a throttle orifice, by way of which said second fluid passage and said pump volume are connected.

17. A prosthetic sphincter device operable by a recipient to control a body duct, the device comprising in operable interconnection:

a fluid-operated inflatable member to close said body duct;

a fluid reservoir;

a pump in fluid communication with said inflatable member and said fluid reservoir to transfer fluid from said inflatable member to said fluid reservoir to deflate said inflatable member and thereby open said body duct; a valve arrangement maintaining said inflatable member normally inflated at least one of said pump and said valve arrangement including an elastomeric sleeve and a bead, the sleeve being resiliently engaged around the bead normally to effect a fluid seal therebetween, the bead being held in a fixed position within said sleeve, and the sleeve being selectively deformable to allow fluid flow between the bead and the sleeve.

18. A device according to claim 17 wherein said bead is provided with a bore for fluid communication between said pump and said inflatable member, a one-way valve being provided to prevent flow through the bore from said pump to said inflatable member.

19. A prosthetic sphincter device operable by a recipient to control a body duct, the device comprising in operable interconnection:

an inflatable fluid-operated occlusion means to close said body duct;

a fluid reservoir;

pump means in fluid communication with said occlusion means and said fluid reservoir to transfer fluid from said occlusion means to said fluid reservoir to deflate said occlusion means and thereby open said body duct; and control means for maintaining said occlusion means normally inflated, at least one of said pump means and said control means including an elastomeric sleeve and a bead, the sleeve being resiliently engaged around the bead normally to effect a fluid seal therebetween, the sleeve being selectively deformable to allow fluid flow between the sleeve and the bead, the bead being provided with a bore for fluid communication between the said pump means and said occlusion means and a one-way valve being provided to prevent flow through the bore from said pump means to said occlusion means.

20. A device according to claim 19, wherein the one-way valve comprises a ball valve.

* * * * *